(12) United States Patent
Feldman et al.

(10) Patent No.: US 7,683,004 B2
(45) Date of Patent: *Mar. 23, 2010

(54) AIR-ACTIVATED ORGANOTIN CATALYSTS FOR POLYURETHANE SYNTHESIS

(75) Inventors: Jerald Feldman, Wilmington, DE (US); Stephan J. McLain, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 1218 days.

This patent is subject to a terminal disclaimer.

(21) Appl. No.: 11/154,387

(22) Filed: Jun. 16, 2005

(65) Prior Publication Data

US 2005/0282700 A1    Dec. 22, 2005

Related U.S. Application Data

(60) Provisional application No. 60/580,235, filed on Jun. 16, 2004.

(51) Int. Cl.
*B01J 21/00* (2006.01)
*B01J 23/00* (2006.01)
*B01J 25/00* (2006.01)
*B01J 29/00* (2006.01)
*B01J 31/00* (2006.01)

(52) U.S. Cl. ............... 502/150; 502/100; 502/152; 502/300; 502/349; 502/352

(58) Field of Classification Search .......... 502/150, 502/100, 152, 300, 349, 352
See application file for complete search history.

(56) References Cited

U.S. PATENT DOCUMENTS 3,083,217 A    3/1963   Sawyer et al.
5,075,468 A  * 12/1991  Frances et al. ............ 556/87
6,187,711 B1   2/2001   Bernard et al.
6,221,494 B1   4/2001   Barsotti et al.
6,649,557 B1  11/2003   Bernard et al.

FOREIGN PATENT DOCUMENTS

EP    0 890 576 A2    1/1999
EP    1 354 903 A1   10/2003

OTHER PUBLICATIONS

F. Hostettler et. al., Organotin Compounds in Isocyanate Reactions, Ind. Eng. Chem., 1960, pp. 609-610, vol. 52.
B. Jousseaume et. al., Air Activated Organotin Catalysts for Silicone Curing and Polyurethane Preparation, Organometallics, 1994, pp. 1034-1038, vol. 13.
M. Kosugi et. al., Preparation and Some Properties of Acyltin Compounds, Bull. Chem. Soc. Jpn., 1987, p. 3462-3464, vol. 60.
A.K. Sawyer, Some Reactions of Organotin Hydrides With Organotin Oxides and Alkoxides, J. Am. Chem. Soc., 1965, pp. 537-539, vol. 87.

* cited by examiner

*Primary Examiner*—Jerry Lorengo
*Assistant Examiner*—James E Mcdonough
(74) *Attorney, Agent, or Firm*—Brian J Myers

(57) ABSTRACT

This invention relates to an organotin-based catalyst system for polyurethane synthesis that is useful in coatings applications. The catalyst has low activity in the absence of oxygen. When a coating mixture comprising the catalyst is sprayed and/or applied to a substrate as a thin film in air, the catalyst is activated. For solvent-based refinish systems comprising hydroxyl and isocyanate species at high solids levels, the catalyst system therefore provides extended viscosity stability, i.e., pot life.

2 Claims, No Drawings

AIR-ACTIVATED ORGANOTIN CATALYSTS FOR POLYURETHANE SYNTHESIS

FIELD OF INVENTION

This invention relates to organotin-based catalyst systems that are useful in coatings applications, and to latent, air-activated catalysts for polyurethane synthesis. The latent catalyst has low activity in the absence of oxygen.

TECHNICAL BACKGROUND

The present invention relates to the use of tin derivatives as polycondensation catalysts. The use of tin salts as polycondensation catalysts has been known for several decades. See F. Hostettler and E. F. Cox (1960) Ind. Eng. Chem. 52:609. These derivatives are used in particular for the condensation of silicones and for the production of polyurethanes.

In the last few years demand has increased for coating systems capable of both extended viscosity stability, that is pot life, and high productivity. High productivity refers to the ability to produce the desired polymer, or polycondensate, as quickly as possible under the implementation conditions, for example, in automotive refinish applications.

For environmental reasons, governmental agencies and users complying with governmental regulations worldwide have exerted pressure to develop coating systems having lower levels of volatile organic compounds (VOC's). A key to resolving these issues is through the dramatic reduction or the elimination of solvents used in coatings. However, reducing the amount of solvent will negatively affect pot life, if cure times remain constant, unless a latent catalyst system is developed.

Jousseaume, B. et al., ("Air Activated Organotin Catalysts for Silicone Curing and Polyurethane Preparation" (1994) Organometallics 13:1034), and Bernard, J. M. et al. (U.S. Pat. No. 6,187,711) describe the use of distannanes as latent catalysts, e.g. $Bu_2(AcO)SnSn(OAc)Bu_2$. Upon exposure to air, such species oxidize to give distannoxanes, e.g. $Bu_2(AcO)SnOSn(OAc)Bu_2$, which are known to be highly active for urethane formation. However, the carboxylate-substituted distannanes are themselves catalysts for the reaction, and have been reported to be "relatively stable in air", which suggests that oxidation to form an active catalyst is slow. See U.S. Pat. No. 3,083,217 to Sawyer et al. UV light appears to be necessary in order to induce oxidation at an appreciable rate in these distannanes. Thus, there exists a need for a catalyst precursor that, in the absence of air, is a very poor catalyst and yet, upon exposure to air, rapidly forms a highly active catalyst that allows for rapid cure.

SUMMARY OF INVENTION

The present invention provides a latent catalyst, the catalytic activity of which is greatly increased when a coating mixture comprising the catalyst is sprayed and/or applied to a substrate as a thin film in an oxygen containing atmosphere, e.g. air. For solvent-based coating systems comprising hydroxyl and isocyanate species at high solids levels, the latent catalyst system provides extended viscosity stability, i.e., pot life, prior to application.

The present catalyst includes tin compounds that are inert or relatively inactive until the coating is actually applied to the substrate in an oxygen containing atmosphere. The present tin catalyst, when placed under coating application conditions, e.g. spraying with a spray gun, undergoes a chemical reaction to yield derivatives that are active under these conditions.

Moreover, in one aspect of the present invention, in subjecting the present catalyst derivatives to oxygen, they provide further present derivatives that are also active as polycondensation catalysts. Another aspect of the present invention is to provide extended pot life coating mixtures that rapidly condense under the conditions of application.

This invention provides a first embodiment of a catalyst having the formula of $R^1_a R^2_b R^3_c Sn[CH(OH)R^4]_d$ or of $R^1_a R^2_b R^3_c Sn[C(O)R^4]_d$, or of mixtures thereof. $R^1$, $R^2$, and $R^3$ are independently hydrogen, optionally substituted hydrocarbyl, optionally substituted aryl, halide, silyl, carboxylate, hydroxide, alkoxide, stannoxy or stannyl group. $R^4$ represents an optionally substituted hydrocarbyl or optionally substituted aryl group. a, b, and c are independently 0, 1, 2, or 3; d is 1 or 2; and a+b+c+d=4.

Also provided is a second embodiment of a catalyst that comprises a first and a second compound. The first compound has the formula previously disclosed above. The second compound has the formula $R_e-Y_n-R_f$, wherein n=an integer between 2 and 8. $R_e$ and $R_f$ are independently hydrogen, optionally substituted hydrocarbyl, optionally substituted aryl, halide, alkoxide, amide, or carboxylate group, or together represent a single bond which ensures the formation of a cyclic structure with n≧3. The radicals Y independently represent a tin-containing chain unit with the structure represented in Formula (I):

(I)

wherein $R_g$ and $R_h$ are independently hydrogen, optionally substituted hydrocarbyl, or optionally substituted aryl.

The invention also provides a system comprising two parts A and B in which Part A comprises an isocyanate species and Part B comprises a polyol and a catalyst described above as the first embodiment. In a different system embodiment Part A comprises a polyol and part B comprises an isocyanate and a catalyst, described above as the first embodiment described above.

Also provided is another system comprising the same parts A and B as previously disclosed. That is, in one embodiment Part A comprises an isocyanate species and Part B comprises a polyol and a first embodiment catalyst. In another embodiment, Part A comprises a polyol species and Part B comprises an isocyanate and a first embodiment catalyst. All embodiments of this system further comprise a second compound of the formula $R_e-Y_n-R_f$, wherein n=an integer between 2 and 8. $R_e$ and $R_f$ are independently hydrogen, optionally substituted hydrocarbyl, optionally substituted aryl, halide, alkoxide, amide, or carboxylate group, or together represent a single bond which ensures the formation of a cyclic structure with n≧3, and the radicals Y independently represent a tin-containing chain unit with the structure represented in Formula (I);

(I)

wherein $R_g$ and $R_h$ are independently hydrogen, optionally substituted hydrocarbyl, or optionally substituted aryl.

The present invention also provides compounds having the formula $R^1{}_2[CH(OH)R^2]SnSn[CH(OH)R^2]R^1{}_2$, wherein $R^1$ is an optionally substituted hydrocarbyl and $R^2$ represents an optionally substituted aryl group. Another compound provided has the formula $R^1{}_2[CH(OH)R^2]SnSnR^1{}_2Sn[CH(OH)R^2]R^1{}_2$, which has a central tetravalent Sn atom bound to two other tetravalent Sn atoms, wherein $R^1$ is an optionally substituted hydrocarbyl and $R^2$ represents an optionally substituted aryl group. A further compound provided has the formula $R^1{}_2Sn[CH(OH)R^2]_2$, wherein $R^1$ is an optionally substituted hydrocarbyl and $R^2$ represents an optionally substituted aryl group.

The present invention provides coatings that comprise the present catalysts and compounds in all the variations described above. The present coatings may be dissolved in at least one solvent and may be a clear, pigmented, metallized, basecoat, monocoat and/or primer coating composition. The present coating may be applied to a variety of substrates.

Besides the catalysts, compositions and coatings, the present invention also provides a process comprising the steps of:

(a) providing a catalyst of the formula selected from the group consisting of $R^1{}_aR^2{}_bR^3{}_cSn[CH(OH)R^4]_d$ and $R^1{}_aR^2{}_bR^3{}_cSn[C(O)R^4]_d$ and mixtures thereof, wherein
$R^1$, $R^2$, and $R^3$ are independently hydrogen, optionally substituted hydrocarbyl, optionally substituted aryl, halide, silyl, carboxylate, hydroxide, alkoxide, stannoxy or stannyl group,
$R^4$ represents an optionally substituted hydrocarbyl or optionally substituted aryl group; a, b, and c are independently 0, 1, 2, or 3,
d is 1 or 2, and
a+b+c+d=4;

(b) contacting at least one isocyanate with the catalyst of step (a) to form a blend;

(c) contacting the blend of step (b) to at least one polyol to form a mixture;

(d) optionally exposing the mixture of step (c) to air or a gas comprising oxygen.

An alternative aspect is that at least one polyol is contacted with the catalyst of step (a) to form a blend, followed by contacting the blend with at least isocyanate.

Another embodiment comprises the steps of (a) providing a catalyst comprising:
  (i) a first compound of the formula selected from the group consisting of $R^1{}_aR^2{}_bR^3{}_cSn[CH(OH)R^4]_d$, and $R^1{}_aR^2{}_bR^3{}_cSn[C(O)R^4]_d$, and mixtures thereof, wherein
  $R^1$, $R^2$, and $R^3$ are independently hydrogen, optionally substituted hydrocarbyl, optionally substituted aryl, halide, silyl, carboxylate, hydroxide, alkoxide, stannoxy or stannyl group,
  $R^4$ represents an optionally substituted hydrocarbyl or optionally substituted aryl group,
    a, b, and c are independently 0, 1, 2, or 3,
    d is 1 or 2, and
    a+b+c+d=4, and
  (ii) a second compound of the formula $R_e$—$Y_n$—$R_f$, wherein
    n=an integer between 2 and 8,
    $R_e$ and $R_f$ are independently hydrogen, optionally substituted hydrocarbyl, optionally substituted aryl, halide, alkoxide, amide, or carboxylate group, or together represent a single bond which ensures the formation of a cyclic structure with n≧3, and the radicals Y independently represent a tin-containing chain unit with the structure represented in Formula (I),

wherein $R_g$ and $R_h$ are independently hydrogen, optionally substituted hydrocarbyl, or optionally substituted aryl;

(b) contacting at least one isocyanate with the catalyst of step (a) to form a blend;

(c) contacting the blend of step (b) to at least one polyol to form a mixture;

(d) optionally exposing the mixture of step (c) to air or a gas comprising oxygen.

The present invention also provides a process for making a coating that comprises providing a present compound or catalyst; optionally adding an additive to form a mixture; optionally dissolving the present compound or catalyst into at least one solvent to form a mixture; and applying either the compound or catalyst or resultant mixture to a substrate.

DETAILED DESCRIPTION OF THE INVENTION

As used herein, "polymers" refer to entities with number average molecular weight from about 100 to about 100,000. Preferably, the number average molecular weight of the polymers is from about 100 to about 10000.

As used herein, "oligomers" refer to polymers that have a number average molecular weight less than about 3000.

As used herein, "air" is defined as an oxygen containing gas.

This invention describes the use of alpha-hydroxystannane compounds as catalysts for formation of crosslinked polyurethanes from polyols and isocyanates. The tin-based catalysts are of the general formula:

wherein $R^1$, $R^2$, and $R^3$ are independently hydrogen, optionally substituted hydrocarbyl, optionally substituted aryl, halide, silyl, carboxylate, hydroxide, alkoxide, stannoxy or stannyl group;

$R^4$ represents an optionally substituted hydrocarbyl or optionally substituted aryl group;

a, b, and c are independently 0, 1, 2, or 3;

d is 1 or 2; and a+b+c+d=4.

This invention also discloses a second class of catalysts; namely, tin-based acylstannane compounds of the general formula:

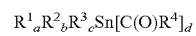

wherein $R^1$, $R^2$, and $R^3$ are independently hydrogen, optionally substituted hydrocarbyl, optionally substituted aryl, halide, silyl, carboxylate, hydroxide, alkoxide, stannoxy or stannyl group;

$R^4$ represents an optionally substituted hydrocarbyl or optionally substituted aryl group; a, b, and c are independently 0, 1, 2, or 3;

d is 1 or 2; and a+b+c+d=4.

It has been found that some catalysts of the above formula are far more active for the crosslinking of multifunctional alcohols and isocyanates to give polyurethanes in the presence of oxygen (air) than in its absence. For example, catalysts of the formula

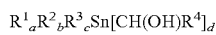

where $R^4$ is optionally substituted aryl are air sensitive and relatively more active for polyurethane synthesis in the presence of oxygen.

While not wishing to be bound by a particular theory, it is hypothesized that upon exposure to air the tin complex is oxidized by molecular oxygen to give a tin carboxylate, which is highly active for the crosslinking reaction between the polyol and the isocyanate. For example, air oxidation of the alpha-hydroxybenzylstannane compound shown below results in formation of the corresponding tin benzoate, which is a crosslinking catalyst. Other side products, such as benzaldehyde, are also formed.

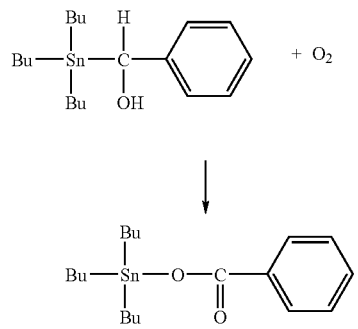

Alpha-hydroxystannane oxidation to give a carboxylate does not appear to have been noted previously. However, examples of acylstannane oxidation are known in the literature. See Kosugi, M. et al. (1987) Bull. Chem. Soc. Jpn. 60:3462, reporting:

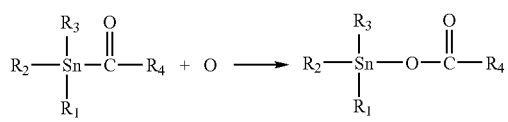

It has been found that acylstannanes are more active catalysts for the crosslinking reaction of multifunctional alcohols and isocyanates to form polyurethanes in the presence of oxygen (air) than in its absence.

The present invention contemplates the use of the alpha-hydroxystannane compounds and the acylstannane compounds in combination with compounds containing Sn—Sn bonds. This invention discloses an improved catalytic activity for polyurethane formation from polyol and isocyanate when the alpha-hydroxystannane compounds are used in combination with compounds comprising tin-tin bonds over the catalytic activity of either catalyst taken individually for the same reaction. The invention also discloses an improved catalytic activity for polyurethane formation from polyol and isocyanate when the acylstannane compounds are used in combination with compounds comprising tin-tin bonds over catalytic activity of either catalyst taken individually for the same reaction.

The compounds containing tin-tin bonds have the general formula:

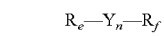

wherein n=an integer between 2 and 8;

$R_e$ and $R_f$ are independently hydrogen, optionally substituted hydrocarbyl, optionally substituted aryl, halide, alkoxide, amide, or carboxylate group, or together represent a single bond which ensures the formation of a cyclic structure with $n \geq 3$; and the radicals Y independently represent a tin-containing chain unit with the structure represented in Formula (I);

$$R_g-\underset{\underset{|}{|}}{Sn}-R_h \qquad (I)$$

wherein $R_g$ and $R_h$ are independently hydrogen, optionally substituted hydrocarbyl, or optionally substituted aryl.

A preferred compound comprising tin-tin bonds is given below:

Another preferred compound comprising tin-tin bonds is given below:

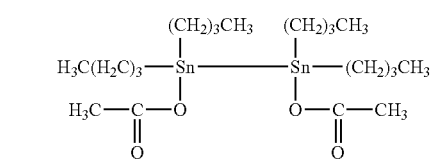

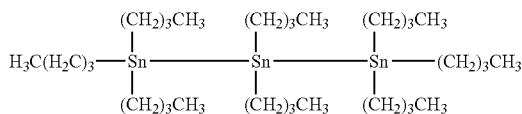

U.S. Pat. No. 6,187,711B1 describes compounds with tin-tin bonds and is hereby incorporated herein by reference. The synergistic effect of Sn—C(O)R or Sn—CH(OH)R in combination with compounds containing Sn—Sn bonds to give more active catalysts is surprising and unexpected. The present invention also contemplates that preferred compounds comprising tin-tin bonds or a tin-containing chain unit may comprise cyclohexyl in the $R_g$ and phenyl in the $R_h$ positions, respectively.

This invention provides acylstannanes as latent air-activated catalysts, and as catalysts in the general sense for the reaction of polyols with isocyanates. Further, this invention discloses alpha-hydroxystannanes as crosslinking catalysts or curing catalysts, latent or otherwise.

This invention also provides alpha-hydroxystannanes, particularly alpha-hydroxybenzylstannanes, and acylstannanes that have improved catalytic activity in the presence of distannanes and air.

On the other hand, as disclosed by this invention, in the absence of air or oxygen, they can have reduced catalytic activity. Thus, exposure to air, e.g. by spraying with a spray gun, results in the desired step-change in activity.

Polyols are generally defined as polymeric or oligomeric organic species with at least two hydroxy functionalities. An example of the isocyanate with functional groups capable of reacting with hydroxyl is as follows:

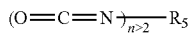

wherein $R_5$ is a hydrocarbyl structure.

Examples of suitable polyisocyanates include aromatic, aliphatic or cycloaliphatic di-, tri- or tetra-isocyanates, including polyisocyanates having isocyanurate structural units, such as, the isocyanurate of hexamethylene diisocyanate and isocyanurate of isophorone diisocyanate; the adduct of 2 molecules of a diisocyanate, such as, hexamethylene diisocyanate and a diol such as, ethylene glycol; uretidiones of hexamethylene diisocyanate; uretidiones of isophorone diisocyanate or isophorone diisocyanate; the adduct of trimethylol propane and meta-tetramethylxylene diisocyanate.

Additional examples of suitable polyisocyanates include 1,2-propylene diisocyanate, trimethylene diisocyanate, tetramethylene diisocyanate, 2,3-butylene diisocyanate, hexamethylene diisocyanate, octamethylene diisocyanate, 2,2,4-trimethyl hexamethylene diisocyanate, 2,4,4-trimethyl hexamethylene diisocyanate, dodecamethylene diisocyanate, omega, omega-dipropyl ether diisocyanate, 1,3-cyclopentane diisocyanate, 1,2-cyclohexane diisocyanate, 1,4-cyclohexane diisocyanate, isophorone diisocyanate, 4-methyl-1,3-diisocyanatocyclohexane, trans-vinylidene diisocyanate, dicyclohexylmethane-4,4'-diisocyanate, 3,3'-dimethyl-dicyclohexylmethane4,4'-diisocyanate, a toluene diisocyanate, 1,3-bis(1-isocyanatol-methylethyl)benzene, 1,4-bis(1-isocyanato-1-methylethyl)benzene, 1,3-bis(isocyanatomethyl)benzene, xylene diisocyanate, 1,5-dimethyl-2,4-bis(isocyanatomethyl)benzene, 1,5-dimethyl-2,4-bis(2-isocyanatoethyl)benzene, 1,3,5-triethyl-2,4-bis(isocyanatomethyl)benzene, 4,4'-diisocyanatodiphenyl, 3,3'-dichloro-4,4'-diisocyanatodiphenyl, 3,3'-diphenyl-4,4'-diisocyanatodiphenyl, 3,3'-dimethoxy-4,4'-diisocyanatodiphenyl, 4,4'-diisocyanatodiphenylmethane, 3,3'-dimethyl-4,4'-diisocyanatodiphenyl methane, a diisocyanatonaphthalene, polyisocyanates having isocyanaurate structural units, the adduct of 2 molecules of a diisocyanate, such as, hexamethylene diisocyanate or isophorone diisocyanate, and a diol such as ethylene glycol, the adduct of 3 molecules of hexamethylene diisocyanate and 1 molecule of water (available under the trademark Desmodur® N from Bayer Corporation of Pittsburgh, Pa.), the adduct of 1 molecule of trimethylol propane and 3 molecules of toluene diisocyanate (available under the trademark Desmodur® L from Bayer Corporation), the adduct of 1 molecule of trimethylol propane and 3 molecules of isophorone diisocyanate, compounds such as 1,3,5-triisocyanato benzene and 2,4,6-triisocyanatotoluene, and the adduct of 1 molecule of pentaerythritol and 4 molecules of toluene diisocyanate.

A specific example of an isocyanate capable of reacting with hydroxyl groups is Desmodur® 3300 from Bayer. The idealized structure of Desmodur® 3300 is given as follows (also, pentamer, heptamer and higher molecular weight species can be present):

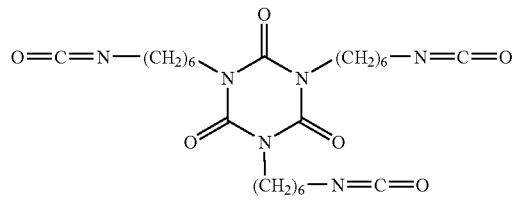

In any of the compositions herein, the polymeric materials may range from relatively low to relatively high molecular weight. It is preferred that they be of relatively low molecular weight so as to keep the viscosity of the compositions before crosslinking low, so as to avoid or minimize the need for solvent(s).

Other materials, which may optionally be present in the compositions and processes, include one or more solvents (and are meant to act only as solvents). These preferably do not contain groups such as hydroxyl or primary or secondary amino.

The present compositions, and the process for making them crosslinked, are useful as encapsulants, sealants, and coatings, especially transportation (automotive) and industrial coatings. As transportation coatings, the present compositions are useful as both OEM (original equipment manufacturer) and automotive refinish coatings. They may also be used as primer coatings. They often cure under ambient conditions to tough hard coatings and may be used as one or both of the so-called base coat and clear coat automotive coatings. This makes them particularly useful for repainting of transportation vehicles in the field.

Depending on use, the compositions and the materials used in the present processes may contain other materials. For example, when used as encapsulants and sealants, the compositions may contain fillers, pigments, and/or antioxidants.

When used as coatings, the present compositions contain typically added ingredients known in the art, which are described below. In particular there may be other polymers (especially of low molecular weight, "functionalized oligomers") which are either inert or have functional group other than hydroxyl or isocyanate and also react with other reactive materials in the coating composition.

Representative of the functionalized oligomers that can be employed as components or potential crosslinking agents of the coatings are the following:

Hydroxyl Oligomers: The reaction product of multifunctional alcohols such as pentaerythritol, hexanediol, trimethylol propane, and the like, with cyclic monomeric anhydrides such as hexahydrophthalic anhydride, methylhexahydrophthalic anhydride, and the like produce acid oligomers These acid oligomers are further reacted with monofunctional epoxies such as butylene oxide, propylene oxide, and the like to form hydroxyl oligomers.

Silane Oligomers: The above hydroxyl oligomers further reacted with isocyanato propyltrimethoxy silane.

Epoxy Oligomers: The diglycidyl ester of cyclohexane dicarboxylic acid, such as Araldite® CY-184 from Ciba Geigy, and cycloaliphatic epoxies, such as ERL®-4221, and the like from Union Carbide.

Aldimine Oligomers: The reaction product of isobutyraldehyde with diamines such as isophorone diamine, and the like.

Ketimine Oligomers: The reaction product of methyl isobutyl ketone with diamines such as isophorone diamine.

Melamine Oligomers: Commercially available melamines such as CYMEL® 1168 from Cytec Industries, and the like.

AB-Functionalized Oligomers: Acid/hydroxyl functional oligomers made by further reacting the above acid oligomers with 50%, based on equivalents, of monofunctional epoxy such as butylene oxide or blends of the hydroxyl and acid oligomers mentioned above or any other blend depicted above.

CD-Functionalized Crosslinkers: Epoxy/hydroxyl functional crosslinkers such as the polyglycidyl ether of Sorbitol DCE-358® from Dixie Chemical or blends of the hydroxyl oligomers and epoxy crosslinkers mentioned above or any other blend as depicted above.

The compositions of this invention may additionally contain a binder of a noncyclic oligomer, i.e., one that is linear or aromatic. Such noncyclic oligomers can include, for instance, succinic anhydride- or phthalic anhydride-derived moieties in hydroxyl oligomers.

Preferred functionalized oligomers have weight average molecular weight not exceeding about 3,000 with a polydispersity not exceeding about 1.5; more preferred oligomers have molecular weight not exceeding about 2,500 and polydispersity not exceeding about 1.4; most preferred oligomers have molecular weight not exceeding about 2,200, and polydispersity not exceeding about 1.25. Other additives also include polyaspartic esters, which are the reaction product of diamines, such as, isopherone diamine with dialkyl maleates, such as, diethyl maleate.

The coating compositions may be formulated into high solids coating systems dissolved in at least one solvent. The solvent is usually organic. Preferred solvents include aromatic hydrocarbons such as petroleum naphtha or xylenes; ketones such as methyl amyl ketone, methyl isobutyl ketone, methyl ethyl ketone or acetone; esters such as butyl acetate or hexyl acetate; and glycol ether esters such as propylene glycol monomethyl ether acetate.

The coating compositions can also contain a binder of an acrylic polymer of weight average molecular weight greater than 3,000, or a conventional polyester such as SCD®-1040 from Etna Product Inc. for improved appearance, sag resistance, flow and leveling and such. The acrylic polymer can be composed of typical monomers such as acrylates, methacrylates, styrene and the like and functional monomers such as hydroxy ethyl acrylate, glycidyl methacrylate, or gamma methacrylylpropyl trimethoxysilane and the like.

The coating compositions can also contain a binder of a dispersed acrylic component which is a polymer particle dispersed in an organic media, which particle is stabilized by what is known as steric stabilization. Hereafter, the dispersed phase or particle, sheathed by a steric barrier, will be referred to as the "macromolecular polymer" or "core". The stabilizer forming the steric barrier, attached to this core, will be referred to as the "macromonomer chains" or "arms".

The dispersed polymer contains about 10 to 90%, preferably 50 to 80%, by weight, based on the weight of the dispersed polymer, of a high molecular weight core having a weight average molecular weight of about 50,000 to 500,000. The preferred average particle size is 0.1 to 0.5 microns. The arms, attached to the core, make up about 10 to 90%, preferably 10 to 59%, by weight of the dispersed polymer, and have a weight average molecular weight of about 1,000 to 30,000, preferably 1,000 to 10,000. The macromolecular core of the dispersed polymer is comprised of polymerized acrylic monomer(s) optionally copolymerized with ethylenically unsaturated monomer(s). Suitable monomers include styrene, alkyl acrylate or methacrylate, ethylenically unsaturated monocarboxylic acid, and/or silane-containing monomers. Such monomers as methyl methacrylate contribute to a high Tg (glass transition temperature) dispersed polymer, whereas such "softening" monomers as butyl acrylate or 2-ethylhexylacrylate contribute to a low Tg dispersed polymer. Other optional monomers are hydroxyalkyl acrylates or methacrylates or acrylonitrile. Optionally, the macromolecular core can be crosslinked through the use of diacrylates or dimethacrylates such as allyl methacrylate or post reaction of hydroxyl moieties with polyfunctional isocyanates. The macromonomer arms attached to the core can contain polymerized monomers of alkyl methacrylate, alkyl acrylate, each having 1 to 12 carbon atoms in the alkyl group, as well as glycidyl acrylate or glycidyl methacrylate or ethylenically unsaturated monocarboxylic acid for anchoring and/or crosslinking. Typically useful hydroxy-containing monomers are hydroxy alkyl acrylates or methacrylates as described above.

The coating compositions can also contain conventional additives such as pigments, stabilizers, rheology control agents, flow agents, toughening agents and fillers. Such additional additives will, of course, depend on the intended use of the coating composition. Fillers, pigments, and other additives that would adversely affect the clarity of the cured coating may not typically be included if the composition is intended as a clear coating.

The coating compositions are typically applied to a substrate by conventional techniques such as spraying, electrostatic spraying, roller coating, dipping or brushing. The present formulations are particularly useful as a clear coating for outdoor articles, such as automobile and other vehicle body parts. The substrate is generally prepared with a primer and or a color coat or other surface preparation prior to coating with the present compositions.

A layer of a coating composition is cured under ambient conditions in the range of 30 minutes to 24 hours, preferably in the range of 30 minutes to 3 hours to form a coating on the substrate having the desired coating properties. One of skill in the art appreciates that the actual curing time depends upon the thickness of the applied layer and on any additional mechanical aids, such as, fans that assist in continuously flowing air over the coated substrate to accelerate the cure rate. If desired, the cure rate may be further accelerated by baking the coated substrate at temperatures generally in the range of from about 60° C. to 150° C. for a period of about 15 to 90 minutes. The foregoing baking step is particularly useful under OEM (Original Equipment Manufacture) conditions.

Catalysts of this invention can be used for coating applications and generally in areas where curing of polyurethane is required, for example in the adhesive industry and related applications. These compositions are also suitable as clear or pigmented coatings in industrial and maintenance coating applications.

The coating composition of the present invention is suitable for providing coatings on variety of substrates. The present composition is especially suitable for providing clear coatings in automotive OEM or refinish applications typically used in coating auto bodies. The coating composition of the present invention can be formulated in the form of a clear coating composition, pigmented composition, metallized coating composition, basecoat composition, monocoat composition or a primer. The substrate is generally prepared with a primer and or a color coat or other surface preparation prior to coating with the present compositions.

Suitable substrates for applying the coating composition of the present invention include automobile bodies, any and all items manufactured and painted by automobile sub-suppliers, frame rails, commercial trucks and truck bodies, including but not limited to beverage bodies, utility bodies, ready mix concrete delivery vehicle bodies, waste hauling vehicle bodies, and fire and emergency vehicle bodies, as well as any potential attachments or components to such truck bodies, buses, farm and construction equipment, truck caps and covers, commercial trailers, consumer trailers, recreational vehicles, including but not limited to, motor homes, campers, conversion vans, vans, pleasure vehicles, pleasure craft snow mobiles, all terrain vehicles, personal watercraft, motorcycles, bicycles, boats, and aircraft. The substrate further includes industrial and commercial new construction and maintenance thereof; cement and wood floors; walls of commercial and residential structures, such office buildings and homes; amusement park equipment; concrete surfaces, such as parking lots and drive ways; asphalt and concrete road surface, wood substrates, marine surfaces; outdoor structures, such as bridges, towers; coil coating; railroad cars; printed circuit boards; machinery; OEM tools; signage; fiberglass structures; sporting goods; golf balls; and sporting equipment.

| ABBREVIATIONS | |
|---|---|
| MEK | methyl ethyl ketone |
| Me | the methyl group—$CH_3$ |
| Bu | the butyl group—$CH_2CH_2CH_2CH_3$ |
| Ph | phenyl group |
| THF | tetrahydrofuran |
| BuLi | butyl lithium |
| DBTDL | dibutyltin dilaurate |
| LDA | lithium diisopropylamide |
| TPO | thermoplastic olefin |

EXPERIMENTAL EXAMPLES

A BK speed drying recorder conforming to ASTM D 5895 was used to measure the drying times of coatings generated using the above-disclosed catalysts. The 12-hour setting was used. In the examples below, the "Stage 3" time corresponds to the surface-dry time when the track made by the needle transitions from an interrupted track to a smooth thin surface scratch. "Stage 4" time corresponds to the final drying time when the needle no longer penetrates the film surface. Gel time corresponds to the time in minutes following activation at which flow is no longer observed in a coating mixture.

The swell ratio of a free film, removed from a sheet of TPO, was determined by swelling the film in methylene chloride. The free film was placed between two layers of aluminum foil and using a LADD punch, a disc of about 3.5 mm in diameter was punched out of the film and the foil was removed from the film. The diameter of the unswollen film ($D_o$) was measured using a microscope with a 10× magnification and a filar lens. Four drops of methylene chloride were added to the film and the film was allowed to swell for two seconds and then a glass slide was placed over the film and the swollen film diameter ($D_s$) was measured. The swell ratio was then calculated as follows:

$$\text{Swell Ratio} = (D_s)^2/(D_o)^2$$

The change in film hardness of the coating was measured with respect to time by using a Persoz hardness tester Model No. 5854 (ASTM D4366), supplied by Byk-Mallinckrodt, Wallingford, Conn. The number of oscillations (referred to as Persoz number) were recorded. Hardness was measured using a Fischerscope® hardness tester (the measurement is in Newton per $mm^2$).

MEK solvent resistance was measured as follows. A coated panel was rubbed (100 times) with an MEK (methyl ethyl ketone) soaked cloth using a rubbing machine. Any excess MEK was wiped off. The panel was rated from 1-10. A rating of 10 means no visible damage to the coating. A rating of 9 means about 1 to 3 distinct scratches. A rating of 8 means about 4 to 6 distinct scratches. A rating of 7 means 7 to 10 distinct scratches. A rating of 6 means 10 to 15 distinct scratches with slight pitting or slight loss of color. A rating of 5 means 15 to 20 distinct scratches with slight to moderate pitting or moderate loss of color. A rating of 4 means scratches start to blend into one another. A rating of 3 means only a few undamaged areas between blended scratches. A rating of 2 means no visible signs of undamaged paint. A rating of 1 means complete failure i.e., bare spots are shown. The final rating was obtained by multiplying the number of rubs by the rating.

Water spot rating is a measure of how well the film is crosslinked early in the curing of the film. If water spot damage is formed on the film, this is an indication that the cure is not complete and further curing of the film is needed before the film can be wet-sanded or buffed or moved from the spray both.

The water spot rating was determined in the following manner: Coated panels are laid on a flat surface and deionized water was applied with a pipette at 1 hour timed intervals. A drop about ½ inch in diameter was placed on the panel and allowed to evaporate. The spot on the panel was examined for deformation and discoloration. The panel was wiped lightly with cheesecloth wetted with deionized water. This was followed by lightly wiping the panel dry with the cloth. The panel was then rated on a scale of 1 to 10. A rating of 10 was considered the best, i.e., there was no evidence of spotting or distortion of discoloration. A rating of 9 meant that water spotting barely detectable. A rating of 8 meant that there was a slight ring as a result of water spotting. A rating of 7 meant that there was very slight discoloration or slight distortion as a result of water spotting. A rating of 6 meant that there was a slight loss of gloss or slight discoloration as a result of water spotting. A rating of 5 meant that there was a definite loss of gloss or discoloration as a result of water spotting. A rating of 4 meant that there was a slight etching or definite distortion as a result of water spotting. A rating of 3 meant that there was a light lifting, bad etching or discoloration as a result of water spotting. A rating of 2 meant that there was a definite lifting as a result of water spotting. A rating of 1 meant that the film dissolved as a result of the water spotting.

As used in the following examples, "Polyol 1" comprised the structure shown below as 50% solids dissolved in methyl amyl ketone, butyl acetate, and propylene glycol methyl ether acetate.

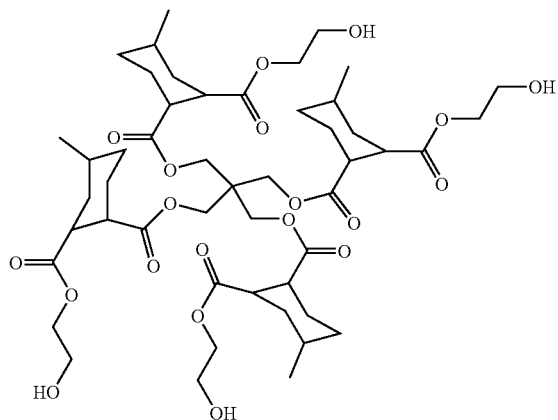

Polyol 1

The isocyanate species used in the examples below was Desmodur 3300A, an oligomer of hexamethylene diisocyanate which is commercially available from Bayer Incorporated, 100 Bayer Road, Pittsburgh, Pa. 15205-9741.

Example 1

Synthesis and Purification of $Bu_3SnCH(OH)Ph$

This example demonstrates the synthesis and purification of the alpha-hydroxystannane complex $Bu_3SnCH(OH)Ph$. Under nitrogen, a dry 250 mL round bottom flask was charged with 2.0 M isopropyl magnesium chloride in diethyl ether (20.6 mL, 41.2 mmol). An additional 15 mL of diethyl ether was then added. To this stirred solution was added tributyl tin hydride (10.0 g, 34.4 mmol) dropwise over a period of 10-15 min. The resulting reaction mixture was heated to reflux, stirred for 1 h, and then cooled down to about 0° C. Benzaldehyde (4.0 g, 37.8 mmol) was then added dropwise over a period of approximately 10 min while maintaining the temperature at about 0° C. The resulting reaction mixture was then heated to reflux and stirred for 1 h before cooling back down to room temperature. The reaction was then quenched by addition of approximately 15 mL aqueous ammonium chloride under nitrogen. The resulting mixture was filtered through a glass frit and the solids were extracted with diethyl ether. The combined organic extracts were concentrated under vacuum and filtered through Florisil™. The Florisil™ pad was washed further with hexane. The combined organic extracts were concentrated under vacuum to afford an oil. Chromatography on silica gel using 95/5 hexane/ethyl acetate as the eluent afforded 3.95 g of $Bu_3SnCH(OH)Ph$ as a pale yellow oil. $^1H$ NMR ($CDCl_3$) δ 7.2 (t, 2H, $H_{meta}$), 7.1 d (d, 12H, $H_{ortho}$), 7.0 (t, 1H, $H_{para}$), 5.1 [d, 1H, CH(OH)], 1.7 [d, 1H, CH(OH)], 1.4-0.7 (m, 27H, Bu's); $^{119}Sn$ NMR ($CDCl_3$) δ −25.0 relative to $SnMe_4$; $^{13}C$ NMR ($CDCl_3$) δ 147.8 ($C_{ipso}$), 128.4 ($C_{ortho}$ or $C_{meta}$), 124.6 ($C_{para}$), 122.9 $C_{ortho}$ or $C_{meta}$), 71.3 [CH(OH)], 28.9 and 27.4 ($CH_2$'s), 13.6 ($CH_3$), 9.1 ($CH_2$).

Example 2

Air-Activation of $Bu_3SnCH(OH)Ph$

This experiment demonstrates the potential of the alpha-hydroxystannane complex $Bu_3SnCH(OH)Ph$ as an air-activated latent catalyst for crosslinking of polyurethane films. Under nitrogen, $Bu_3SnCH(OH)Ph$ (250 mg, 0.63 mmol) was dissolved in a mixture of polyol 1 (23.7 g) and Desmodur 3300A (9.7 g). A portion of the resulting mixture was transferred to a vial with a stir-bar and stirred under nitrogen at ambient temperature. The remaining portion was removed from the glove box and was exposed to air. A sample of the air-exposed material was used to coat two 12 inch×1 inch glass test strips for BK dry time tests (film thicknesses of 75 and 150 μm were used). A stir-bar was added to the remaining air-exposed material and it was stirred under air at ambient temperature.

It was found that the air-exposed material gelled after 2.25 h. On the other hand, the material stirred under nitrogen required 7 h to gel. Thus, gelation occurred much faster under air. In the BK dry time tests, stage 4 dry times of 3.5 h (75 μm) and 3.9 h (150 μm) were observed.

Example 3

Air-Activation of $Me_3SnC(O)Ph$

This experiment demonstrates that the acylstannane complex $Me_3SnC(O)Ph$ is an air-activated latent catalyst for crosslinking of polyurethane films. $Me_3SnC(O)Ph$ was synthesized by the procedure originally described in Mitchell, T. N. et al. (1990), Synthesis, 1001. Under nitrogen, $Me_3SnC(O)Ph$ (250 mg, 0.93 mmol) was dissolved in a mixture of polyol 1 (23.7 g) and Desmodur 3300A (9.7 g). A portion of the resulting mixture was transferred to a vial with a stir-bar and stirred under nitrogen at ambient temperature. The remaining portion was removed from the glove box and was exposed to air. A sample of the air-exposed material was used to coat two 12 inch×1 inch glass test strips for BK dry time tests (film thicknesses of 75 and 150 :m were used). A stir-bar was added to the remaining air-exposed material and it was stirred under air at ambient temperature.

It was found that the air-exposed material gelled after 4.5 h. On the other hand, the material stirred under nitrogen required 13 h to gel. Thus, gelation occurred much faster under air. In the BK dry time tests, stage 4 dry times of 7.1 h (75 μm) and 6.5 h (150 μm) were observed.

Examples 4-5

Air-Activation of an Alpha-Hydroxystannane and a Tritin Compound

Example 4 contained both tin compounds, an alpha-hydroxystannane and a tritin compound. Example 5 contained only the alpha-hydroxystannane compound $Bu_3SnCH(OH)Ph$. These experiments demonstrate that the combination of the alpha-hydroxystannane complex $Bu_3SnCH(OH)Ph$ with the tritin complex $Bu_3SnSn(Bu)_2SnBu_3$ is an air-activated latent catalyst for crosslinking of polyurethane films that has higher activity than $Bu_3SnCH(OH)Ph$ alone. $Bu_3SnCH(OH)Ph$ was synthesized according to the procedure outlined in Example 1. $Bu_3SnSn(Bu)_2SnBu_3$ was synthesized by the procedure originally described in Sawyer, A. K. (1965) J. Am. Chem Soc., 87:537-9. In a nitrogen filled drybox, polyol 1 (11.87 g) and Desmodur® 3300A (4.84 g) were combined. Aliquots of stock solutions of the catalysts (0.10M in butyl acetate) were added to the polyol/Desmodur® solution and mixed to give a homogeneous solution (Table 1). 2 mL aliquots of the solution were transferred to two septum-capped vials. The vials were removed from the dry-box and one was opened and exposed to the air for several minutes and recapped and shaken. Both vials were placed in a constant temperature bath at 25° C. The two samples were examined regularly and the gel times under nitrogen and air were recorded. The remaining solution was removed from the dry-box and exposed to air. It was used to coat two 12 inch×1 inch glass test strips for BK dry time tests (film thicknesses of 75 μm).

TABLE 1

|  | Example 4 (both compounds) | Example 5 (alpha-hydroxystannane compound only) |
|---|---|---|
| $Bu_3SnSn(Bu)_2SnBu_3$ (micromole) | 11.4 |  |
| $Bu_3SnCH(OH)Ph$ (micromole) | 18.7 | 52.9 |
| gel time (hours under $N_2$) | >>6.5 | >6.5 |
| gel time (hours under air) | 6.5 | >6.5 |
| BK test (stage 3, min) | 301 | >690 |

In examples 4 and 5 the molar amounts of Sn were the same. Example 4 showed faster gelation in air than under nitrogen. Based upon the BK stage 3 times, the sample containing both Sn compounds cured more rapidly (Example 4) than the samples containing only $Bu_3SnCH(OH)Ph$ (Example 5).

Examples 6-7

Air-Activation of an Alpha-Hydroxystannane and a Ditin Compound

These experiments demonstrate that the combination of the alpha-hydroxystannane complex $Bu_3SnCH(OH)Ph$ with the ditin complex $Bu_2(CH_3CO_2)Sn$—$Sn(O_2CCH_3)Bu_2$, is an air-activated latent catalyst for crosslinking of polyurethane films that has higher activity than $Bu_3SnCH(OH)Ph$ alone.

$Bu_3SnCH(OH)Ph$ was synthesized according to Example 1. $Bu_2(CH_3CO_2)Sn$—$Sn(O_2CCH_3)Bu_2$ was synthesized by the "Second Method" described in Jousseaume, B. et al. (1994) Organometallics 13:1034. The experimental procedures for preparing samples for the gel time test and BK 3 recorder test were identical to Examples 4-5. The results (Table 2) show that the combination of the ditin complex with a relatively small amount of $Bu_3SnCH(OH)Ph$ (Example 6) gave a faster gel time under air than under nitrogen, and resulted in much faster curing than $Bu_3SnCH(OH)Ph$ alone which at this concentration gave no detectable curing (Example 7).

TABLE 2

|  | Example 6 | Example 7 |
|---|---|---|
| $Bu_2(CH_3CO_2)Sn$—$Sn(O_2CCH_3)Bu_2$ (micromole) | 114 |  |
| $Bu_3SnCH(OH)Ph$ (micromole) | 18.8 | 22.2 |
| gel time (hours under $N_2$) | 5.5 | >24 |
| gel time (hours under air) | 3 | >24 |
| BK test (stage 4, min) | 402 | >660* |

*Curing did not reach stage 3 in this time

Example 8

Synthesis and Purification of $Bu_3SnC(O)Ph$

This example demonstrates the synthesis and purification of the acylstannane complex $Bu_3SnC(O)Ph$. In a nitrogen-filled glove box, a 250 mL three-neck round bottom flask was charged with diisopropylamine (1.31 g, 13.0 mmol) and 40 mL dry THF. The solution was cooled to about −30° C. and 2.5 M BuLi in hexane (5.2 mL, 13.0 mmol) was added slowly by syringe. The reaction mixture was allowed to warm to room temperature. A dropping funnel containing $Bu_3SnCH(OH)Ph$ (5.00 g, 12.6 mmol) dissolved in 20 mL dry THF, a nitrogen inlet, and a glass stopper were attached to the round bottom flask. The apparatus was removed from the glove box. The reaction setup was connected to a nitrogen-filled Schlenk line. The reaction mixture was cooled to about −78° C., and the $Bu_3SnCH(OH)Ph$/THF solution was added dropwise. After the addition, the reaction mixture was allowed to stir for 15-20 min at −78° C., during which time the color changed from yellow to light orange. The glass stopper was then removed, and 1,1'-(azo dicarbonyl)dipiperidine (3.18 g, 12.6 mmol) was quickly added as a solid. The resulting reaction mixture was allowed to stir for 20-30 min at −78° C., during which time the reaction mixture turned dark orange. The reaction mixture was allowed to warm to about 0° C., and stirred for approximately 30 min at that temperature. The reaction was quenched at 0° C. by the addition of approximately 14 mL saturated ammonium chloride; solids formed in the reaction mixture. The reaction mixture was brought into a nitrogen-filled glove-box, filtered, dried ($MgSO_4$), and concentrated to afford an orange oil. Chromatography on silica gel using 95/5 hexane/ethyl acetate as the eluent afforded 1.80 g of $Bu_3SnC(O)Ph$ as a yellow-orange oil. $^1H$ NMR ($C_6D_6$) δ 7.9 (2H, d, $H_{ortho}$), 7.3 (3H, mult, $H_{meta}$ & $H_{para}$), 1.8-0.9 (27H, Bu's); $^{119}Sn$ NMR ($CDCl_3$) δ 87.4 relative to $SnMe_4$; $^{13}C$ NMR ($CDCl_3$) δ 244.8 (CO), 142.9, 132.8, 128.8, 127.7 ($C_{aromatic}$), 29.1, 27.3, 13.6, 11.5 ($C_{butyl}$).

Example 9

Air Activation of $Bu_3SnC(O)Ph$

This example demonstrates that the acylstannane complex $Bu_3SnC(O)Ph$ is an air-activated latent catalyst for crosslinking of polyurethane films. Under nitrogen, $Bu_3SnC(O)Ph$ (250 mg, 0.63 mmol) was dissolved in a mixture of polyol 1 (23.7 g) and Desmodur® 3300A (9.7 g). A portion of the resulting mixture was transferred to a vial with a stir-bar and stirred under nitrogen at ambient temperature. The remaining portion was removed from glove-box and exposed to air. A sample of the air-exposed material was used to coat a 12 inch×1 inch glass test strip for BK dry time tests (a film thickness of 150 μm was used). A stir-bar was added to the remaining air-exposed material and it was stirred under air at ambient temperature. It was found that the air-exposed material gelled after 1.4 h; the material stirred under nitrogen required 4.5 h to gel. Thus, gelation occurred faster under air. In the BK dry time test, a stage 4 dry time of 2.2 h was observed.

Example 10

Preparation of the "Crude" Alpha-Hydroxystannane Complex of Examples 12, 14, 17 & 19

This example demonstrates the preparation of the "crude" alpha-hydroxystannane complex used in examples 12, 14, 17 and 19 below. Under nitrogen, a round bottom flask was charged with 2.0 M isopropyl magnesium chloride in diethyl ether (41 mL, 82.0 mmol) and an additional 20 mL of diethyl ether was added. To this stirred solution was added tributyltin hydride (20.0 g, 68.7 mmol), dropwise, over a period of approximately 15 min. The resulting reaction mixture was heated to reflux, stirred for 1 h, and then cooled down to about 0° C. Benzaldehyde (12.0 g, 113.1 mmol) was then added dropwise over a period of approximately 15 min while maintaining the temperature at about 0° C. The resulting orange reaction mixture was then heated to reflux and stirred for 1 h before cooling back down to room temperature. The reaction was then quenched by addition of approximately 10 mL aqueous ammonium chloride under nitrogen; solids precipitated from the reaction mixture. The resulting mixture was filtered through a glass frit and the solids extracted with diethyl ether. The combined organic extracts were concentrated under vacuum and filtered through Florisil™. The Florisil™ pad was washed further with hexane. The combined organic extracts were concentrated under vacuum to afford 29.8 g of an orange oil that was used in Examples 12, 14, 17 and 19 without further purification.

Coating Mixtures Prepared for Examples 11-15

The coating mixtures used for Examples 11-15 are shown below. The quantities are in grams. For each of the examples, the constituents of Portion 1 were charged into a mixing vessel in the order shown above and mixed; then Portion 2 was charged into the mixing vessel and thoroughly mixed with Portion 1 to form each of examples. Each of the coating compositions was applied with a doctor blade over a separate phosphated cold roll steel panel primed with a layer of PowerCron® Primer supplied by PPG, Pittsburgh, Pa., to a dry coating thickness of 50 micrometers and air dried at ambient temperature conditions. The panels were then tested using the tests shown in Table 3.

|  | Example: | |
| --- | --- | --- |
|  | 11 | 12 |
| Portion 1 | | |
| Oligomer 1# | 30 | 30 |
| Butyl Acetate | 14.8 | 12.62 |
| Flow Additive* | 0.44 | 0.44 |
| DBTDL solution** | 2.17 | 0 |
| 10% crude Bu$_3$SnCH(OH)Ph*** in Butyl Acetate | 0 | 4.35 |
| Portion 2 | | |
| Tolonate ® HDT***** | 19.47 | 19.47 |

|  | Example: | | |
| --- | --- | --- | --- |
|  | 13 | 14 | 15 |
| Portion 1 | | | |
| Oligomer 1# | 30 | 30 | 30 |
| Butyl Acetate | 14.8 | 13.72 | 12.62 |
| Flow Additive* | 0.44 | 0.44 | 0.44 |
| DBTDL solution** | 2.17 | 0 | 0 |
| 10% crude Bu$_3$SnCH(OH)Ph*** in Butyl Acetate | 0 | 3.25 | 0 |

-continued

|  | Example: | | |
| --- | --- | --- | --- |
|  | 13 | 14 | 15 |
| 10% pure Bu$_3$SnCH(OH)Ph**** in Butyl Acetate | 0 | 0 | 4.35 |
| Portion 2 | | | |
| Tolonate ® HDT***** | 19.47 | 19.47 | 19.47 |

"Oligomer 1" composition is that of procedure #2 of U.S. Pat. No. 6,221,494 B1, but made at 80% solids in Methyl amyl ketone
*20% BYK 301 ® flow additive in Propylene glycol monomethyl ether acetate supplied by BYK-CHEMIE, Wallingford, Connecticut.
**1% Dibutyltin dilaurate in methyl ethyl ketone supplied by Elf-Atochem North America, Inc. Philadelphia, Pennsylvania.
***See Example 10
****See Example 1
*****Tolonate ® HDT Isocyanurate trimer of hexamethylene diisocyanate supplied by RHODIA INC., Cranbury, New Jersey.

Coating Mixtures Prepared for Examples 16-19

The coating mixtures used for Examples 16-19 are shown below. The quantities are in grams. For each of the examples, the constituents of Portion 1 were charged into a mixing vessel in the order shown above and mixed; then Portion 2 was charged into the mixing vessel and thoroughly mixed with Portion 1 to form each of the examples. Each of the coating compositions was applied with a doctor blade over a separate phosphated cold roll steel panel primed with a layer of PowerCron® Primer supplied by PPG, Pittsburgh, Pa., to a dry coating thickness of 50 micrometers and air dried at ambient temperature conditions. The panels were then tested using the tests shown in Table 3.

|  | Example: | | | |
| --- | --- | --- | --- | --- |
|  | 16 | 17 | 18 | 19 |
| Portion 1 | | | | |
| Oligomer 2## | 26.89 | 26.89 | 26.89 | 26.89 |
| Butyl Acetate | 15.21 | 10.96 | 15.21 | 14.14 |
| Flow Additive* | 0.42 | 0.42 | 0.42 | 0.42 |
| DBTDL solution** | 2.12 | 0 | 2.12 | 0 |
| 10% crude Bu$_3$SnCH(OH)Ph*** in Butyl Acetate | 0 | 6.37 | 0 | 3.19 |
| Portion 2 | | | | |
| Tolonate ® HDT***** | 20.36 | 20.36 | 20.36 | 20.36 |

Oligomer 2 is from procedure # 10 of U.S. Pat. No. 6,221,494 B1
*20% BYK 301 ® flow additive in Propylene glycol monomethyl ether acetate supplied by BYK-CHEMIE, Wallingford, Connecticut.
**1% Di butyl tin dilaurate in methyl ethyl ketone supplied by Elf-Atochem North America, Inc. Philadelphia, Pennsylvania.
***See Example 10
****See Example 1
*****Tolonate ® HDT Isocyanurate trimer of hexamethylene diisocyanate supplied by RHODIA INC., Cranbury, New Jersey.

Examples 11-19

Examples 12, 14, 15, 17, and 19 employed the air-activated catalysts of the present invention. Examples 11, 13, 16, and 18 are comparative examples using a conventional dibutyltin dilaurate catalyst. From the comparative data in Table 3 it can be seen that, when used in isocyanate crosslinked coatings, the catalysts of the present invention showed improved early cure properties such as:

Improved BK dry times
Improved water spot resistance
Improved early (4 hour and 1 day) MEK resistance
Improved early (1 day) swell ratios
Equivalent or improved early hardness These improved early cure properties will lead to significantly improved productivity in automotive refinish body shops using ambient cured coatings.

In addition to improved cure properties, the catalysts of the present invention possess improved time to gel; this will result in coatings that have a longer useful "pot life." "Pot life" is the time, after activation, during which a coating can be spray applied to give good appearance and handling in an automotive refinish body shop.

mL graduated cylinder, sealed with a septum, and removed from the dry box. The n-butyl lithium was added by cannula over about 10 min to the isopropyl amine at −45° C. This mixture was stirred 0.5 h. The solution was nearly clear and light yellow.

In the dry box a scintillation vial was charged with 11 g (46.8 mmol) of $Bu_2SnH_2$ and diluted with 25 mL of THF. The LDA solution in a rubber septum-capped flask was maintained at −45° C. in the liquid $N_2$/chlorobenzene bath and the $Bu_2SnH_2$ was added via cannula over 10 min. The entire mixture was maintained at −45° C. for 0.5 h. 5.19 g (49 mmol) of benzaldehyde was charged to a scintillation vial in the drybox and diluted with 20 mL of THF. The vial was septum sealed, removed from the drybox, and the solution was added

TABLE 3

| Test Catalyst | Ex. 11 Oligo*. 1 500 ppm DBTDL | Ex. 12 Oligo. 1 1% crude Bu3SnCH(OH)Ph | Ex. 13 Oligo. 1 500 ppm DBTDL | Ex. 14 Oligo. 1 0.75% crude Bu3SnCH(OH)Ph | Ex. 15 Olig.o 1 1% pure Bu3SnCH(OH)Ph | Ex. 16 Oligo. 2 500 ppm DBTDL | Ex. 17 Oligo. 2 1.5% crude Bu3SnCH(OH)Ph | Ex. 18 Oligo. 2 500 ppm DBTDL | Ex. 19 Oligo. 2 0.75% crude Bu3SnCH(OH)Ph |
|---|---|---|---|---|---|---|---|---|---|
| Cal. Wt. Sol. | 65 | 65 | 65 | 65 | 65 | 65 | 65 | 65 | 65 |
| Time to Gel. (min) | 55 | 70 | 56 | 93 | 120 | 100 | 153 | 143 | 305 |
| BK3 TIME (min) | >600 | 176 | 331 | 189 | 208 | >600 | 196 | 366 | 274 |
| BK4 TIME (min) | >600 | 387 | 441 | 338 | 300 | >600 | >600 | >600 | >600 |
| APP/Clarity | V. Good | V. Good | V. Good | V. Good | V. Good | V. Good | V. Good | V. Good | V. Good |
| WATER SPOT | | | | | | | | | |
| 4 HR RT | 3 | 9 | 8 | 8 | 6 | 3 | 8 | 6 | 7 |
| 1 DAY RT | 5 | 10 | 8.5 | 9 | 9 | 5 | 8.5 | 8 | 8 |
| MEK RUBS | | | | | | | | | |
| 4 HR RT | 100 | 400 | 600 | 500 | 500 | 10 | 300 | 25 | 200 |
| 1 DAY RT | 400 | 800 | 700 | 800 | 800 | 50 | 750 | 700 | 600 |
| 30 DAY RT | 800 | 800 | | | | 800 | 750 | | |
| SWELL RATIO | | | | | | | | | |
| 1 DAY RT | 2.31 | 1.92 | 2.05 | 2.02 | 1.85 | 2.52 | 1.86 | 2.11 | 1.85 |
| 7 DAY RT | 1.76 | 1.66 | 1.77 | 1.75 | 1.75 | 1.82 | 1.63 | 1.75 | 1.67 |
| 30 DAY RT | 1.66 | 1.61 | | | | | 1.65 | 1.66 | |
| PERSOZ HARD | | | | | | | | | |
| 4 DAY RT | tacky | 16 | Tacky | 17 | tacky | Tacky | 21 | tacky | tacky |
| 1 DAY RT | 58 | 85 | 91 | 72 | 184 | 103 | 145 | 168 | hard; slipped off |
| FISHER HARD | | | | | | | | | |
| 1 DAY RT | 7.97 | 10.92 | 10 | 66 | 83 | 11.13 | 50.1 | 28 | 72 |
| 7 DAY RT | 110 | 46 | 44 | 158 | 132 | 136 | 118 | 155 | 153 |
| 30 DAY RT | 155 | 47 | | | | | 167 | 120 | |

*Oligo. is an abbreviation of Oligomer

Example 20

Synthesis of a Mixture of $Bu_2[Ph(OH)CH]SnSn[CH(OH)Ph]Bu_2$, $Bu_2[Ph(OH)CH]SnSn(Bu)_2Sn[CH(OH)Ph]Bu_2$ and $Bu_2Sn[CH(OH)Ph]_2$, and Separation of the Mixture This example illustrates the synthesis of a mixture of three alpha-hydroxybenzyl tin complexes and their separation by column chromatography. Preparation of lithium diisopropylamide (LDA): An oven-dried 250 mL round bottom flask was charged in the dry box with 5.19 g (51.4 mmol) of diisopropylamine and 25 mL of anhydrous THF. The flask was sealed with a rubber septum and removed from the drybox, connected to a nitrogen bubbler, and cooled to −45° C. in a liquid $N_2$/chlorobenzene cooling bath. Separately, 32.2 mL of 1.6 M n-butyl lithium (51.2 mmol) in hexane was charged to a 50 via cannula over 10 min to the −45° C. solution of Sn lithiate solution. This mixture was stirred for 1 h at −45° C. After 20 min the mixture was taken into the dry box and placed in the dry box freezer and stored at −30° C. overnight. The mixture was taken out of the dry box freezer the next morning, charged with 60 mL of nitrogen sparged hexane followed by 60 mL of nitrogen sparged, saturated aqueous $NH_4Cl$. The reaction was stirred briefly, allowed to settle, and decanted. The THF/hexane layer was taken back into the dry box and evaporated to an oil. The oil was extracted into pentane and filtered through a medium glass frit into a tared round bottom flask. The pentane was removed under vacuum to leave a hazy pale yellow oil: 15.5 g. 9.45 g of the crude oil was chromatographed in 2 to 3 g portions as follows. A 12"×1" column filled to 7 inches with silica gel 60, 230-400 mesh, was utilized. Two column eluents were used. The first eluent was comprised of 20% ethyl acetate by volume and 80% hexane by volume. The second eluent was 100% ethyl acetate. The solvents used were reagent grade from EM Sciences and were sparged with dry nitrogen using a fritted glass filter stick over ½ hour to deoxygenate them prior to transport into the dry box and use as eluent. The silica gel was degassed under high vacuum (~20 millitorr) for 16-18 hours before use. The column was packed by pre-mixing the silica gel with the 80/20 hexane ethyl acetate and pouring the slurry into the column. All chromatography was performed in the dry box under nitrogen. The column was eluted by gravity feed and 1-4 mL aliquots of eluent were collected in glass scintillation vials. Progress was monitored using thin layer chromatography on each of the vial aliquots. Two distinct fractions were collected by combining aliquots using the 80/20 hexane/ethyl acetate eluent and a third fraction was obtained by elution with 100% ethyl acetate.

Fraction 1: Mixture of cyclic $(Bu_2Sn)_n$ n=5.6. Net wt.=1.1 g, $^{119}Sn$ NMR ($C_6D_6$, 186.7 MHz): −200.5 (s, $J_{SnSn}$=450 Hz, 471 Hz); −201.4 (s, $J_{SnSn}$=463 Hz)

Fraction 2: Mixture of $Bu_2[Ph(OH)CH]SnSn[CH(OH)Ph]Bu_2$ and $Bu_2[Ph(OH)CH]SnSn(Bu)_2Sn[CH(OH)Ph]Bu_2$, Net wt.=4.08 g, TLC shows traces of the faster eluting cyclic compounds $(Bu_2Sn)_n$ n=5.6 so a portion of fraction 2 was rechromatographed to give cyclic-free material. $^1H$ NMR ($C_6D_6$, 500 MHz): 0.7-1.95 (m, 27H, Bu); 2.6 (s, 0.27H, $J_{SnH}$=66 Hz, CH(O$\underline{H}$)Ph, $Sn_3$ complexes); 3.16, 3.25 (s,s, 0.71H, $J_{SnH}$=66 Hz, CH(O$\underline{H}$)Ph, $Sn_2$ complexes, 1:1 mixture of racemic pair and meso compound); 5.28 (m, 1H, C$\underline{H}$(OH)Ph, $Sn_3$ complexes and $Sn_2$ complexes, 1:1 mixture of racemic pair and meso compound); 6.9-7.5 (m, 7.2H, Ph+$C_6D_5H$). $^{119}Sn$ NMR ($C_6D_6$, 186.7 MHz): −48.15 (s, $Bu_2[Ph(OH)CH]\underline{SnSn}(Bu)_2\underline{Sn}[CH(OH)Ph]Bu_2$, Sn satellites are too small to see); −48.7, −51.5 (s,s, $Bu_2[Ph(OH)CH]\underline{SnSn}[CH(OH)Ph]Bu_2$, $J_{SnSn}$=1674 Hz, 1651 Hz, 1:1 mixture of racemic pair and meso compound); −52.35 (s, $Bu_2[Ph(OH)CH]\underline{SnSn}(Bu)_2Sn[CH(OH)Ph]Bu_2$, Sn satellites too small to see). Based on relative peak heights, the mixture is 88 mole % $Sn_2$ complexes. The proton integration which shows 71 mole % $Sn_2$ complexes is probably more accurate. Reverse Phase HPLC/GC of a mixture of the two compounds allowed separation and identification of the peaks for the dimer and trimer. Column Zorbax Eclipse XDB-C18, 2.1×50 mm, A=water+0.05% trifluoroacetic acid, B=acetonitrile+0.05% trifluoroacetic acid. Program: 95% A to 0% A over 4.5 min, hold 3.5 min, then return to initial conditions, 0.8 mL/min, 60° C., 1 microliter injection. 7.157-7.223 min (897.2, largest peak, $Bu_2[Ph(OH)CH]SnSn(Bu)_2Sn[CH(OH)Ph]Bu_2$—OH), 6.143-6.210 min (663.1, largest peak, $Bu_2[Ph(OH)CH]SnSn[CH(OH)Ph]Bu_2$—OH). Both compounds appear to be protonated and lose $H_2O$ to give a stable cation in the mass spectrometer.

Fraction 3: $Bu_2Sn[CH(OH)Ph]_2$/benzyl alcohol mixture, Net wt.=1.13 g. $^1H$ NMR ($C_6D_6$, 500 MHz): 0.7-2.0 (m, Bu); 2.55, 2.80 (s,s, —CH(O$\underline{H}$)Ph, $J_{SnH}$=60 Hz, 31:69 ratio, mixture of racemic pair and meso compound), 4.30 (s, PhC$\underline{H}_2$OH); 5.25 (s, —C$\underline{H}$(OH)Ph, $J_{SnH}$=21 Hz), 6.8-7.5 (m, $C_6\underline{H}_5C(OH)H+C_6\underline{H}_5CH_2OH+C_6D_5H$). $^{119}Sn$ NMR ($C_6D_6$, 186.7 MHz): −71.0, −71.7 (s,s, 31:69 ratio, mixture of racemic pair and meso compound).

Examples 21-23

Separation of $Bu_2[Ph(OH)CH]SnSn[CH(OH)Ph]Bu_2$, $Bu_2[Ph(OH)CH]SnSn(Bu)_2Sn[CH(OH)Ph]Bu_2$, and Mixtures Thereof In a synthesis similar to Example 20, a large number of fractions were collected in the chromatography and it proved possible to obtain some combined fractions that were pure $Bu_2[Ph(OH)CH]SnSn[CH(OH)Ph]Bu_2$, pure $Bu_2[Ph(OH)CH]SnSn(Bu)_2Sn[CH(OH)Ph]Bu_2$, and a mixture of the two. This allowed separate testing of the $Sn_2$ and $Sn_3$ compounds as well as the mixture. In a nitrogen filled drybox, polyol 1 (4.74 g) and Desmodur® 3300A (1.95 g) were combined. Aliquots of stock solutions of the catalysts in butyl acetate were added to the polyol/Desmodur® solution and mixed to give a homogeneous solution. Aliquots of the solution were transferred to two septum-capped vials. The vials were removed from the dry-box and one was opened and exposed to the air for several minutes and recapped and shaken. Both vials were placed in a constant temperature bath at 25° C. The two samples were examined regularly and the gel times under nitrogen and air were recorded. The remaining solution was removed from the dry-box and exposed to air. It was used to coat 12 inch×1 inch glass test strips for BK dry time tests (film thicknesses of 75 μm).

TABLE 4

|  | Example 21 $\{Bu_2[Ph(OH)CH]Sn\}_2$ 21.7 mg | Example 22 $\{Bu_2[Ph(OH)CH]Sn\}_2\{SnBu_2\}$ 21.7 mg | Example 23 Mixture 21, 22 8.67 mg | Standard DBTDL 2.17 mg |
|---|---|---|---|---|
| gel time (h under $N_2$) | 0.75 | 0.5-0.75 | 0.75-1 | 1-1.3 |
| gel time (h under air) | 3.5-4 | 3.5-4 | 4-5 | NA |
| BK test (stage 4, min) | 57 | 66 | 95 | 215 |

Table 4 shows that the new tin compounds are air-activated latent catalysts, which catalyze curing much more rapidly under air than nitrogen. When compared to DBTDL at concentrations that give roughly comparable gel times under nitrogen, they have longer pot lives under nitrogen and show faster cure on the BK test.

What is claimed is:

1. A catalyst of the formula selected from the group consisting of
$R^1{}_aR^2{}_bR^3{}_cSn[CH(OH)R^4]_d$, $[R^4CH(OH)]_qR^1{}_sR^2{}_tSn(Sn(R^5)(R^6))_uSnR^1{}_vR^2{}_w[CH(OH)R^4]_x$, $[R^4C(O)]_qR^1{}_sR^2{}_tSn(Sn(R^5)(R^6))_uSnR^1{}_vR^2{}_w[C(O)R^4]_x$ and mixtures thereof,
wherein $R^1$, $R^2$, and $R^3$ are independently hydrogen, optionally substituted hydrocarbyl, optionally substituted aryl, halide, silyl, carboxylate, hydroxide, alkoxide group;
$R^4$ represents an optionally substituted hydrocarbyl or optionally substituted aryl group;

$R^5$ and $R^6$ are each independently optionally substituted hydrocarbyl or alkoxide;

a, b, and c are independently 0, 1, 2, or 3;

d is 1 or 2;

each q and x are independently 1 or 2 each s, t, v and w are independently 0, 1 or 2;

u is 0 or 1;

q+s+t=3;

v+w+x=3 and a+b+c+d=4.

2. A catalyst as recited in claim 1, having the formula of $Bu_3SnCH(OH)Ph$.

* * * * *